United States Patent [19]

van Muiden

[11] Patent Number: 5,736,094
[45] Date of Patent: Apr. 7, 1998

[54] METHOD FOR MANUFACTURING A CATHETER WITH VARYING PHYSICAL PROPERTIES ALONG ITS LENGTH

[75] Inventor: Johannes Gerardus Maria van Muiden, Peize, Netherlands

[73] Assignee: Cordis Corporation, Miami, Fla.

[21] Appl. No.: 633,599

[22] Filed: Apr. 17, 1996

[30] Foreign Application Priority Data

Apr. 18, 1995 [NL] Netherlands ............... 1000162

[51] Int. Cl.[6] .................................. B29C 35/10
[52] U.S. Cl. ............ 264/471; 264/171.27; 264/230; 264/295; 604/264
[58] Field of Search .............. 264/470, 1, 171.26, 264/171.28, 150, 230, 471, 295; 425/131.1, 462, 174.4; 604/264

[56] References Cited

U.S. PATENT DOCUMENTS

| 3,861,972 | 1/1975 | Glover et al. ............... 156/86 |
| 4,385,635 | 5/1983 | Ruiz ............................ 128/658 |
| 4,764,324 | 8/1988 | Burnham ..................... 264/150 |
| 4,904,431 | 2/1990 | O'Maleki ..................... 264/149 |
| 5,059,375 | 10/1991 | Lindsay ...................... 264/167 |
| 5,074,845 | 12/1991 | Miraki et al. ................ 604/101 |
| 5,085,649 | 2/1992 | Flynn .......................... 604/282 |
| 5,180,372 | 1/1993 | Vegoe et al. ................ 604/161 |
| 5,348,536 | 9/1994 | Young et al. ............... 264/171.27 |
| 5,458,572 | 10/1995 | Campbell et al. ............ 604/96 |
| 5,549,109 | 8/1996 | Samson et al. ............. 128/642 |
| 5,562,127 | 10/1996 | Fanselow et al. .......... 138/137 |

FOREIGN PATENT DOCUMENTS

WO 84/04664  6/1984  WIPO.

*Primary Examiner*—Jeffery R. Thurlow
*Attorney, Agent, or Firm*—Paul A. Coletti

[57] ABSTRACT

The invention relates to a method for manufacturing a catheter. This method includes the manufacturing of a tube-like basic body with a proximal and a distal end, the arranging of a connecting member to the proximal end, and the finishing of the distal end, wherein for the basic body at least partially material has been used which forms cross links when irradiated and wherein the basic body is exposed to controlled radiation.

8 Claims, 4 Drawing Sheets

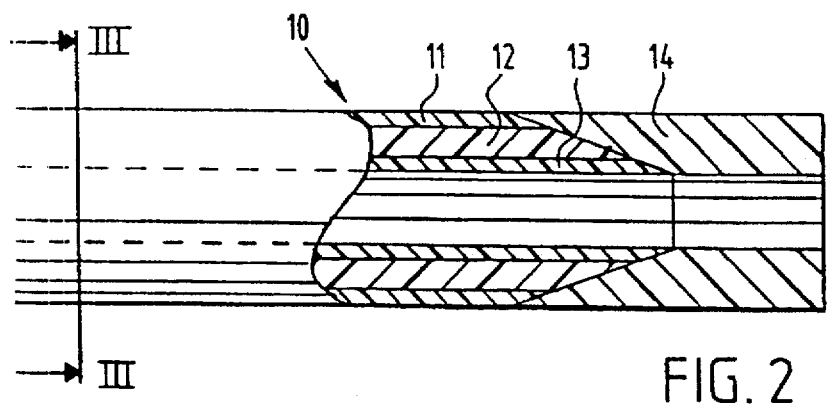 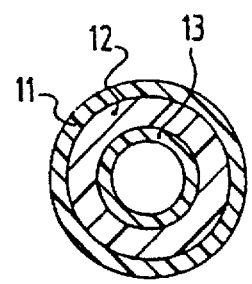
FIG. 2  FIG. 3
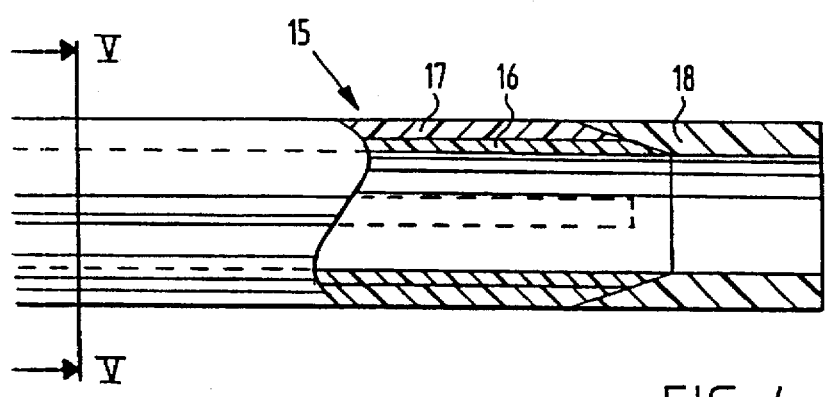 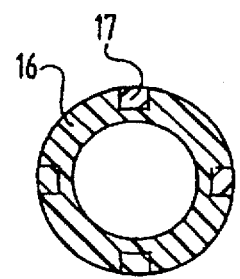
FIG. 4  FIG. 5
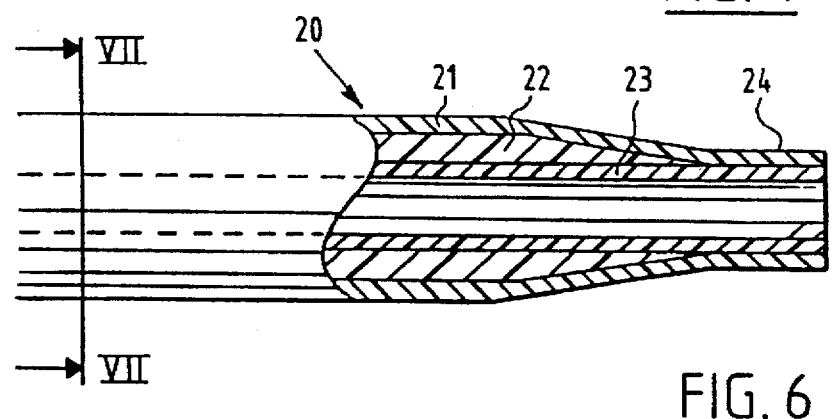 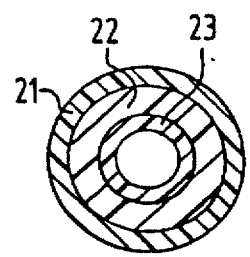
FIG. 6  FIG. 7
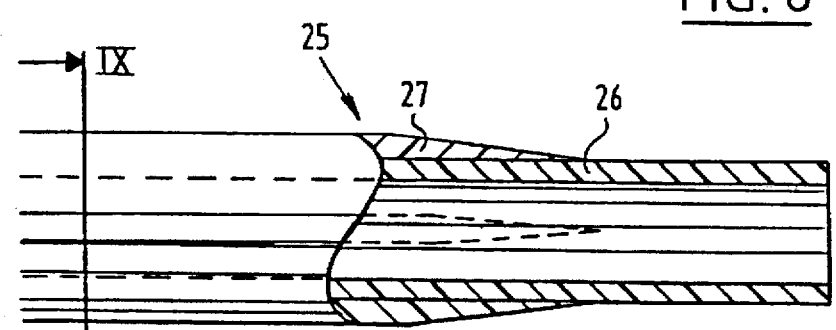 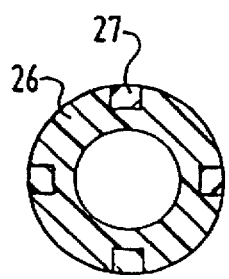
FIG. 8  FIG. 9

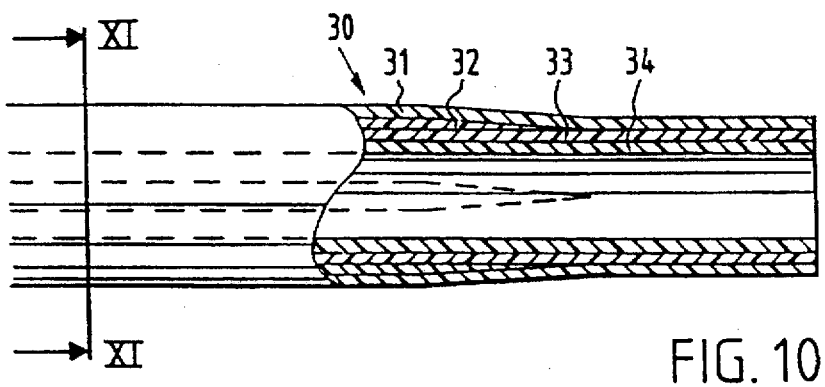 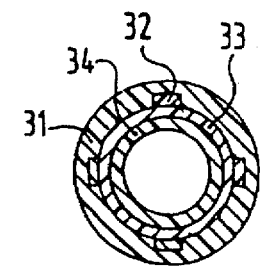
FIG. 10  FIG. 11
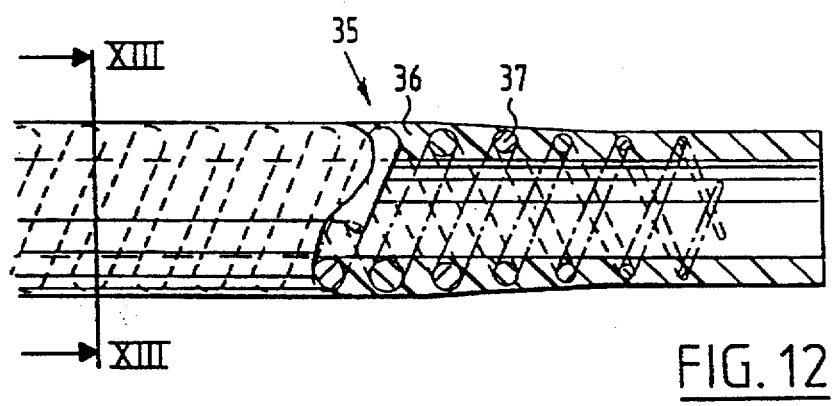 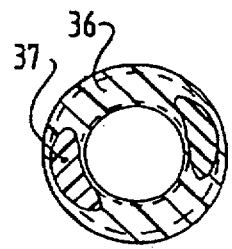
FIG. 12  FIG. 13
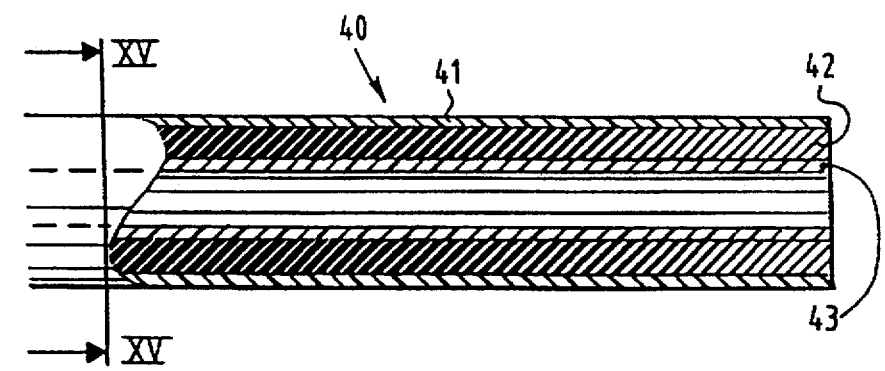 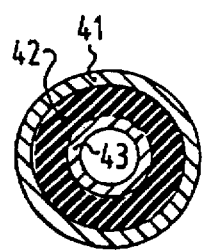
FIG. 14  FIG. 15
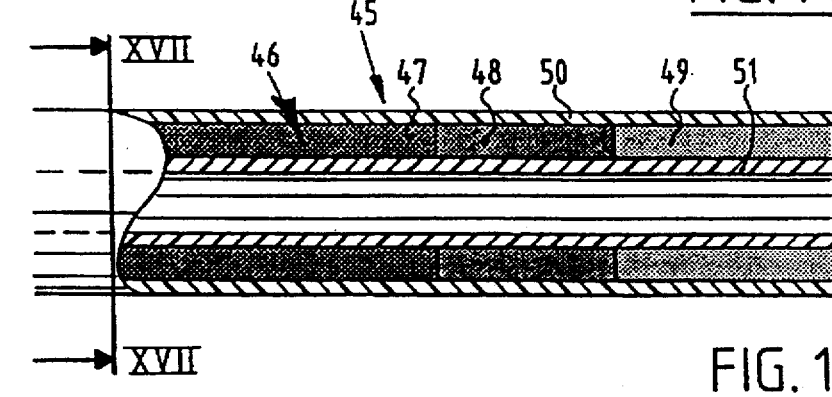 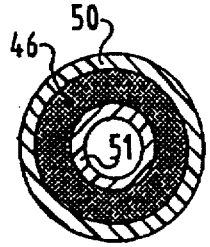
FIG. 16  FIG. 17

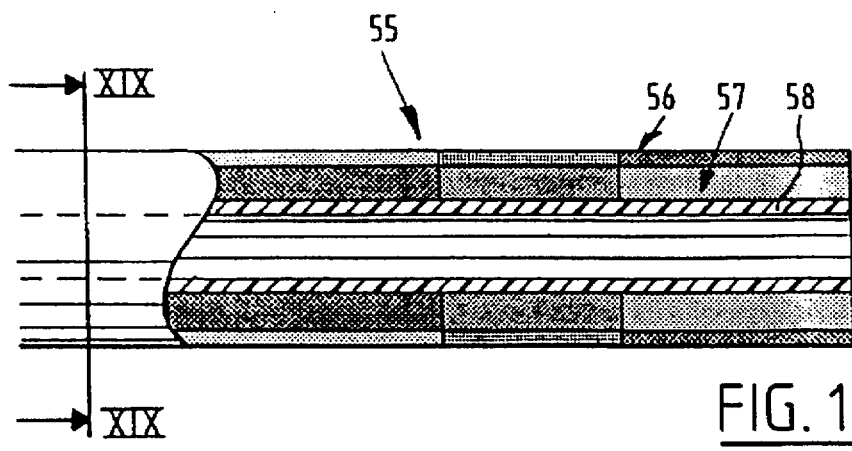
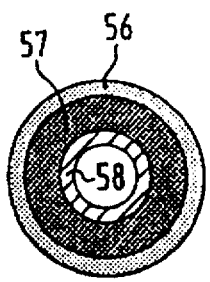
FIG. 18   FIG. 19
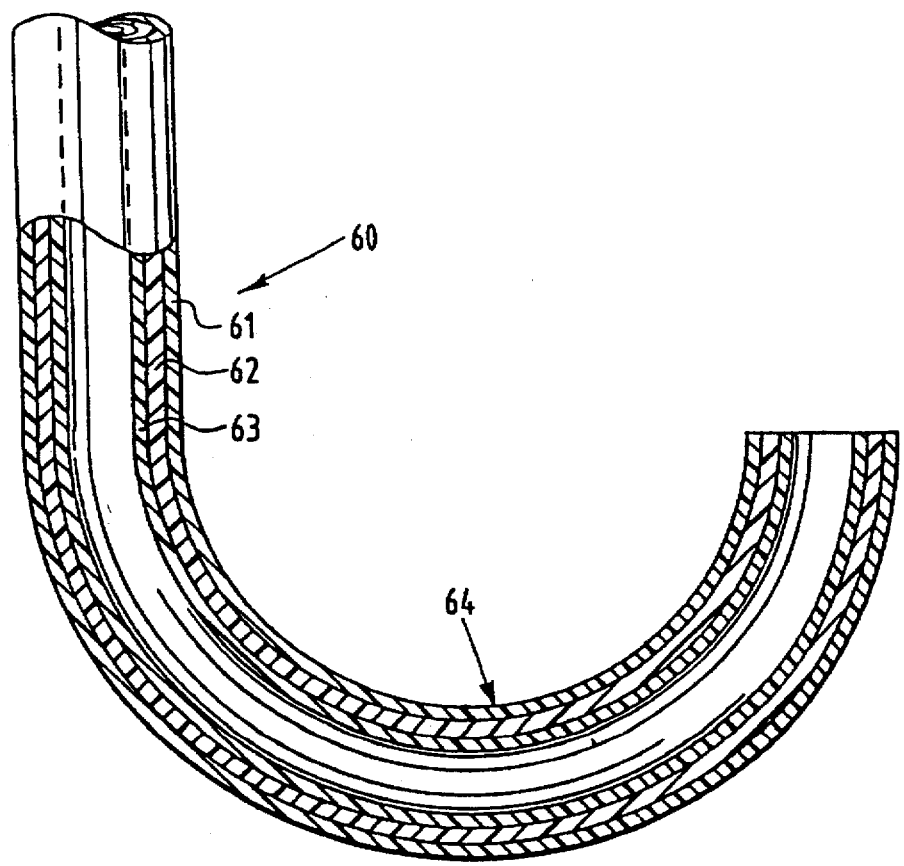
FIG. 20

METHOD FOR MANUFACTURING A CATHETER WITH VARYING PHYSICAL PROPERTIES ALONG ITS LENGTH

FIELD OF THE INVENTION

The invention relates to a method for manufacturing a catheter with varying physical properties along its length. A catheter, such as for instance a catheter used for anglographic purposes, should be sufficiently stiff in order to introduce it into a patient; at the same time torsion resistant, so that the physician carrying out the procedure can rotate the catheter longitudinally in order to maneuver the end-section into a certain position; as a rule pressure resistant; and should also be relatively soft and pliable at the tip in order to avoid trauma when introducing and using the catheter. Consequently it is desirable that the catheter has varying properties in a longitudinal direction. The relatively proximal section should preferably be stiff and pressure resistant and the stiffness can be reduced towards the distal end.

SUMMARY OF THE INVENTION

The object of the invention is to provide a method with which the desired variation in properties can be achieved.

The invention relates to a method for manufacturing a catheter. This method comprises the manufacturing of a tube-like basic body with a proximal and a distal end, the arranging of a connecting member to the proximal end, and the finishing of the distal end, wherein for the basic body at least partially material has been used which forms cross links when irradiated and wherein the basic body is exposed to controlled radiation.

This aim is achieved with the method disclosed herein. The mechanical properties of the material forming cross links when irradiated very strongly with the number of cross links. With a great number of cross links the material will be relatively stiff and have a great tensile strength, whereas the material will be pliable when there are few cross links. With the method according to the invention each section of the catheter can be give the required properties.

Preferably, the layers surrounding the central layer form a seal preventing oxidation of the material forming the cross links during irradiation. In addition, materials forming cross links often comprise additives which influence the formation of the cross links, which additives, such as for instance isocyanate monomers or acrylic monomers with peroxide initiators, are often not bio-compatible, so that direct contact with the body of the patient should be avoided.

In particular when the basic body is formed by co-extrusion of different materials, the thickness of the layer of material forming the cross links can easily be reduced to near zero towards the distal end by turning off the supply of this material either gradually or, if desired abruptly, during the extrusion process. Another suitable embodiment of the method is then characterized herein. Depending on the degree of irradiation the strips form more or less stiff longitudinal ridges in the basic body. The basic body will thus obtain a high degree of pliability coupled with significant pressure resistance.

A suitable further development is also characterized. The more radiation absorbing material is added, the less transparent the cross link-forming-material becomes for the radiation, so that less cross links will be formed. A variation in the material properties can thus be effected with a constant radiation.

Another possibility if further disclosed. The more additive added, the more cross links will be formed with a certain radiation intensity and/or duration and consequently the material will become stiffer and stronger.

A suitable further development is also characterized. By altering the material properties as a result of the radiation, the particular shape is "frozen", so that in this manner simply pre-formed catheters can be manufactured.

DESCRIPTION OF THE DRAWINGS

The invention will be explained in greater detail in the following description with reference to the attached drawings.

FIGS. 2–19 show each time pairs of partial longitudinal and transverse cross-sections of different versions of an embodiment; and FIG. 20 illustrates a section of a catheter manufactured with the method according to the invention.

DETAILED DESCRIPTION OF THE INVENTION

Figure 1:
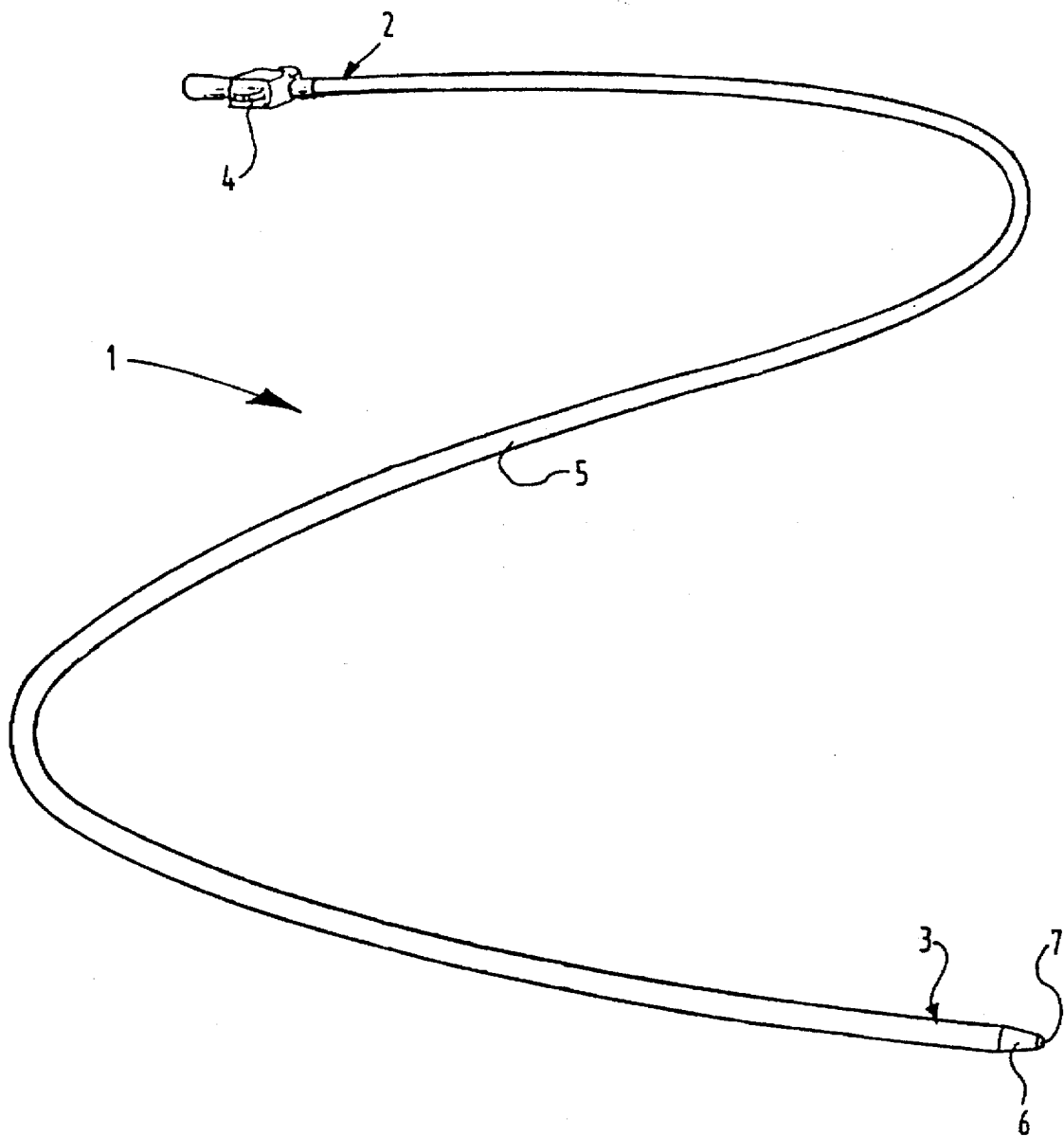
FIG. 1 illustrates a catheter manufactured with the method according to the invention.

FIG. 1 shows a catheter 1 manufactured with the method according to the invention. This catheter is obtained by manufacturing a tube-like basic body 5 with a proximal end 2 and a distal end 3. At the proximal end 2 a connecting member 4 has been arranged by means of which a connection can be effected with the lumen 7 of the catheter 1.

The catheter 1 has been finished by arranging an end-section 6, made of a soft material, at the distal end 3.

For the basic body 5, at least partly, material has been used which forms cross links when exposed to radiation and the basic body 5 has been subjected to controlled radiation, so that in this material cross links have been formed in a controlled manner which have resulted in the required material properties.

Plastic materials forming cross links are known as such. Because of additives in the polymers, links are formed between the molecule chains of the plastic material under the influence of high energetic irradiation, such as UV, electron-beam or gamma radiation. The deformability of the plastic material is as a result only minimally diminished, accompanied however by an increase in strength.

With the embodiment of a catheter 10 manufactured with the method according to the invention illustrated schematically in FIG. 2, the basic body has been made so as to comprise three layers 11, 12, 13. The central layer 12 comprises the material forming cross links. The layers 11 and 13 seal the layer 12 from the outside. An end-section 14, which is free of material forming cross links, also seals the layer 12 at the end-surface to which it has been arranged. The catheter basic body formed for instance by co-extrusion and provided with an end-section 14 is exposed to radiation compatible with the material 12, as a result of which the required cross links are formed and the material 12 obtains a greater strength and a somewhat greater stiffness at least locally.

The surrounding layers 11 and 13 and the end-section 14 prevent oxidation of the material of which layer 12 has been made, as it remains separated from oxygen.

In addition one or more additives can have been received in the layer 12, which promote the forming of cross links but which are not biocompatible, so that contact with the body of the patient and/or body fluids is not acceptable. The surrounding layers 11 and 12 and the end-section 14 prevent this contact.

It will be clear that the FIGS. 2 and 3 are schematic representations. The scale in a longitudinal and lateral direction is not necessarily the same.

The catheter 15 of the FIGS. 4 and 5 has another construction. The basic body 15 can also have been manufactured by means of coextrusion of different materials. The material forming the cross links has been arranged here in the form of strips 17 extending in a longitudinal direction. Following radiation these strips form stiffer ridges in the softer basic material 16. Also here an a-traumatic end-section 18, made of a softer material, has been arranged.

As the strips 17 have an external surface, it should be seen to that, following irritation, no residual additives remain which could enter into the vascular system of the patient and consequently could form a risk for the patient.

The catheter 20 of the FIGS. 6 and 7 resembles the one of the FIGS. 2 and 3 considerably. Also in this case the basic body is made up of three layers 21, 22, 23 wherein the central layer 22 comprises the material forming the cross links.

Towards the distal end 24 the thickness of the layer 22 is reduced to zero. This can easily be effected by gradually turning of the supply of the material of which this layer 22 has been made, on extrusion of the basic material. In the end-section 24 the outer layer 21 and the inner layer 23 make contact, so that the layer 22 forming the cross links is also in this case sealed entirely from its surroundings.

With the catheter 25 of the FIGS. 8 and 9, the strip-shaped wall sections 27, which have been received in the basic material 26, have been reduced to zero towards the distal end. Consequently the distal end is made up of basic material 26 which will be relatively soft in the case of this example of an embodiment. The required stiffness is effected by the strips 27 which comprise the material forming the cross links and which have been irradiated. Consequently the initial section of the catheter 25 will have a relatively great stiffness and the end-section a limited stiffness.

The catheter 30 of the FIGS. 10 and 11 is in a way a combination of the previous embodiments. The central layer 33, with the strip-shaped stiffer parts 32 connected to it, are surrounded by an outer layer 31 and an inner layer 34 effecting once again the seal towards the outside.

With the embodiment of the catheter 35, as illustrated in the FIGS. 12 and 13, also a helically shaped strip of material 37 can be formed in the basic material 36 when the basic body is extruded. This helically shaped strip of material 37 may comprise the material forming the cross links, so that the pitch, which will have a greater stiffness and a higher tensile strength following irradiation, can serve as reinforcement for the catheter. As a result the latter will better be able to withstand high pressure inside the lumen, while in addition the torsional resistance is increased. As can be seen in FIG. 12, the thickness of the helically shaped strips of material can be reduced towards the distal end, as a result of which the effect will be diminished, so that a variation of properties in the longitudinal direction is obtained.

As has been mentioned before, the variations of the properties in a longitudinal direction can also be obtained by varying the intensity of the radiation in a longitudinal direction and by consequently varying the number of cross links formed in a longitudinal direction. Such a method is employed when manufacturing the catheter 40 illustrated in the FIGS. 14 and 15. For the purpose of explaining this method the catheter 40 has been illustrated in its most simple form as having been made up of three concentric layers, a central layer 42 comprising the material forming the cross links surrounded by an outer layer 41 and an inner layer 43. The less dense hatching towards the right of the picture indicates that the radiation intensity has been reduced towards the right, as a result of which in the right-hand section of the catheter 40 illustrated in FIG. 14 less cross links have been formed than in the section positioned more towards the left. The right-hand end-section is consequently more pliable than the section positioned more towards the left.

Yet another method has been employed with the catheter 45. Also here a three-layer construction is illustrated. A central layer 46 comprising the material forming the cross links is surrounded by an outer layer 50 and an inner layer 51. As can be seen in FIG. 16, the central layer 46 has been divided into a number of segments 47, 48, 49. Each of these segments comprises another concentration of additives which promote the formation of cross links. The right-hand segment 49 comprises a relatively low concentration of these additives whereas the concentration is higher in the segment 48 and still higher in the segment 47. Thus, on uniform irradiation, that is to say radiation of the same intensity and duration, a varying number of cross links will be formed in the segments 47, 48, and 49, whereby in particular towards the right a decreasing number of cross links per volume unit will be formed, so that the stiffness of the central layer 46 reduces towards the rights.

The catheter 55 illustrated in the FIGS. 18 and 19 has been manufactured with yet another method according to the invention. The three-layer construction has been illustrated here again schematically comprising a central layer 57 surrounded by an outer layer 56 and an inner layer 58. The outer layer 56 is however divided into segments wherein towards the distal end an increasing quantity of filling material has been received which reduces the transparency of the material to the applied radiation. The segment on the very left is consequently the most transparent to the radiation and the right-hand segment the least. On uniform irradiation the central layer 57 will consequently receive a variable radiation intensity, as a result of which varying numbers of cross links will be formed. In particular the left-hand segment, of which the outer layer 56 comprises comparatively little of the additive limiting transparency, will experience a relatively high radiation intensity, whereas the segments positioned more towards the right will receive a decreasing intensity of radiation. Thus the stiffness of the material of the central layer 57 will decrease towards the right following radiation.

FIG. 20 shows a catheter 60, again made up of three layers, namely an intermediate layer 62 comprising material forming cross links, surrounded by an outer layer 61 and an inner layer 63. During irradiation this catheter 60 is held in a bent shape, as a result of which the curve 64 is defined in the material. The cross links are formed while the intermediate layer 62 was kept in the deformed state, as a result of which relative positions of the molecule chains which are part of the deformation are, as it were, fixed by the cross links formed.

It should be noted that the figures only serve as an illustration of the method and indicate in particular the possibilities in which the variations in the material properties of the basic material can be obtained. The figures are consequently not intended to limit the method according the invention to the manufacture of specific catheter constructions.

What is claimed is:

1. Method for manufacturing a catheter comprising the manufacturing of a tubular, general tapered basic body with a proximal and a distal end, the arranging of a connecting member at the proximal end and the finishing of the distal end;

wherein the basic body contains at least some material which crosslinks when exposed to radiation and wherein the basic body is exposed to controlled radiation;

wherein the wall of the basic body is made up of at least three layers and wherein at least a central crosslinked layer comprises the material which crosslinks; and wherein the finishing comprises the arranging of a catheter-end section which is free of material forming crosslinks.

2. Method as claimed in claim 1, wherein the catheter-end-section is formed by reducing the thickness of the crosslinked layer of material which crosslinks tapers so that towards the distal end is free of material forming crosslinks.

3. Method as claimed in claim 1, wherein the basic body is formed by extrusion and the material forming cross links is formed essentially in bands extending longitudinally in the basic body.

4. Method as claimed in claim 3 wherein the bands extend in a helical pattern.

5. Method as claimed in claim 1, wherein the intensity and/or the duration of the radiation of sections in the longitudinal direction of the basic body is varied from the proximal to the distal end, so that the number of crosslinks in the central crosslinked layer varies along the longitudinal axis.

6. Method as claimed in claim 1, wherein the material forming cross links is mixed with in the longitudinal direction of the catheter varying quantities of material absorbing the radiation.

7. Method as claimed in claim 1, wherein the material forming cross links is mixed with in the longitudinal direction of the catheter varying quantities of an additive promoting the formation of cross links.

8. Method as claimed in claim 1, wherein at least a section of the basic body is held bent in a previously determined shape during irradiation.

* * * * *